United States Patent
Redkar et al.

(10) Patent No.: US 6,833,360 B2
(45) Date of Patent: Dec. 21, 2004

(54) PROCESS FOR PREPARING PSEUDOEPHEDRINE TANNATE

(75) Inventors: Sham N. Redkar, Bound Brook, NJ (US); James R. Schleck, Somerset, NJ (US); Vilas M. Chopdekar, Edison, NJ (US)

(73) Assignee: Jame Fine Chemicals, Inc., Bound Brook, NJ (US)

( * ) Notice: Subject to any disclaimer, the term of this patent is extended or adjusted under 35 U.S.C. 154(b) by 0 days.

(21) Appl. No.: 10/326,361

(22) Filed: Dec. 20, 2002

(65) Prior Publication Data

US 2003/0114392 A1 Jun. 19, 2003

Related U.S. Application Data

(63) Continuation-in-part of application No. 10/017,131, filed on Dec. 14, 2001, now Pat. No. 6,677,381.

(51) Int. Cl.[7] .................. A61K 31/7024; C07H 13/02; C07C 69/88
(52) U.S. Cl. .............................. 514/23; 536/119; 560/68
(58) Field of Search ........................... 514/23; 536/119; 560/68

(56) References Cited

U.S. PATENT DOCUMENTS

| | | | |
|---|---|---|---|
| 3,282,789 A | | 11/1966 | Marty et al. ................ 167/82 |
| 5,599,846 A | | 2/1997 | Chopdekar et al. ......... 514/653 |
| 5,663,415 A | * | 9/1997 | Chopdekar et al. .......... 560/68 |
| 6,037,358 A | | 3/2000 | Gordziel ..................... 514/357 |
| 6,287,597 B1 | * | 9/2001 | Gordziel ..................... 424/464 |
| 6,306,904 B1 | | 10/2001 | Gordziel ..................... 514/530 |

FOREIGN PATENT DOCUMENTS

| | | | |
|---|---|---|---|
| JP | 54034814 | 4/1974 | |
| WO | WO 02/05745 A2 | 1/2002 | |
| WO | WO 02/05746 A3 | 1/2002 | ........... C07C/69/88 |
| WO | WO 02/05747 A2 | 1/2002 | |

* cited by examiner

Primary Examiner—Cecilia J. Tsang
Assistant Examiner—Taylor V. Oh
(74) Attorney, Agent, or Firm—Jack Matalon

(57) ABSTRACT

The invention pertains to a method for preparing pseudoephedrine tannate by reacting pseudoephedrine free base at a temperature of about 70 to about 110° C. with tannic acid neat or as an aqueous slurry containing about 5 to about 30 wt. % water.

7 Claims, No Drawings

US 6,833,360 B2

PROCESS FOR PREPARING PSEUDOEPHEDRINE TANNATE

CROSS-REFERENCE TO RELATED APPLICATION

This application is a continuation-in-part of application Ser. No. 10/017,131 filed Dec. 14, 2001 now U.S. Pat. 6,677,381.

FIELD OF THE INVENTION

The invention pertains to a process for preparing pseudoephedrine tannate.

BACKGROUND OF THE INVENTION

Pseudoephedrine, i.e., ($\alpha$S)-$\alpha$-[(1,S)-1-methylamino)ethyl]benzenemethanol, is a well-known nasal decongestant. The compound has a melting point of 118–118.7° C. and has an optical rotation of $[\alpha]_D^{20}$+51.2° in ethanol. Since pseudoephedrine is sparingly soluble in water, it typically is administered in the form of its hydrochloride salt. Pseudoephedrine hydrochloride has the molecular formula $C_{10}H_{15}NO \cdot HCl$, a melting point of 182.5–183.5° C. and has an optical rotation of $[\alpha]_D^{20}$+62.05° in ethanol. The hydrochloride is quite soluble in water (2 grams dissolve in 1 ml of water). It is typically administered to human beings in need of such medication in the form of a nasal spray, tablets and/or suspensions. It frequently is administered in combination with one or more other antihistamine and/or antitussive compositions, e.g., diphenhydramine hydrochloride, chlorpheniramine maleate, dextromethorphan hydrobromide monohydrate, etc.

The currently administered forms of pseudoephedrine, i.e., generally an acid salt such as the hydrochloride or sulfate, are disadvantageous in that they are absorbed very quickly in the mammalian body. Accordingly, although such forms provide prompt relief, multiple doses must be taken on a daily basis to provide an effective level of a medicament over the prescribed period of treatment (generally several days to one week). It would be very desirable if a form of was available that would have extended-release properties, i.e., the pseudoephedrine would be slowly released into the patient's bloodstream over a prolonged period of time. Until recently, the only slow-release forms of pseudoephedrine that were available were those such as polymer-coated tablets. Such prior art formulations provided mixed results in that the pseudoephedrine was not available for adsorption into the patient's bloodstream until the polymeric coating was dissolved, but thereafter the pseudoephedrine was quickly absorbed and metabolized. The result is that frequently, the pseudoephedrine had to again be administered to the patient within the period of only a few hours.

The foregoing problem was solved by converting the pseudoephedrine free base into its tannate salt by reaction of the free base with tannic acid. The tannate salt stabilizes the pseudoephedrine free base and most important, imparts extended release properties to the pseudoephedrine. In recent years, tannate salts of antihistamines have become known, e.g., see U.S. Pat. Nos. 5,599,846; 5,663,415; 6,037,358; 6,287,597; and 6,306,904.

Tannic acid is commercially available and is used in many industrial applications. It is frequently referred to as gallotannic acid, gallotannin, glycerite or tannin. It is a pale tan powder having a decomposition point of 210–215° C., and is highly soluble in water and alcohols. Its molecular formula is $C_{76}H_{52}O_{46}$ and its CAS number is 1401-55-4.

Tannic acid is typically produced from Turkish or Chinese nutgall and has a complex non-uniform chemistry and typically contains about 5–10 wt. % water.

Commercially available antihistamine tannate compositions are relatively impure. Such compositions are typically prepared by reacting the antihistamine free base with tannic acid in the presence of a volatile solvent, usually isopropanol. The yield is only fair (e.g., about 70%) and decomposition products, e.g., 2–5 wt. %, and a significant amount of the volatile solvent, e.g., 6–10 wt. %, based on the weight of the composition, remains with the product and cannot be removed.

Typically, in the conventional isopropanol route, the antihistamine free base and the tannic acid will be present in the isopropanol at a concentration of about 20 wt. %, based on the weight of the reaction mixture. The reaction mixture is stirred for about one hour, while maintaining a temperature of 60–70° C. The reaction mixture is cooled to room temperature and filtered. The precipitate is vacuum dried for an extended period of time at a temperature of 60–80° C. A yield of product of only about 70% is obtained and the product purity will be about 85–90 wt. %, based on the weight of the composition (the impurities consist of isopropanol and decomposition products which cannot be removed).

Many antihistamine tannates are heat sensitive and therefore undergo decomposition quite readily upon prolonged exposures to temperatures as low as 50° C. Accordingly, even when the solvent utilized in its preparation has a relatively high vapor pressure such as is in the case of isopropanol, it is impossible to reduce the solvent content below about 6 wt. %, based on the weight of the antihistamine tannate composition, even at reduced pressures and very mild elevated temperatures. Moreover, from an environmental point, it would be most desirable if the antihistamine tannate could be prepared such that the use of volatile solvents could be avoided.

The process disclosed in U.S. Pat. No. 5,663,415 represents a significant improvement over the isopropanol route. The process disclosed in the '415 patent involves three steps:

(a) the antihistamine in the form of its free base is contacted with tannic acid in the presence of water at a maximum temperature which will not cause decomposition of the antihistamine tannate to an extent of greater than about 5 wt. %, based on the weight of the antihistamine tannate;

(b) the antihistamine is allowed to remain in contact with the tannic acid in the presence of water for a period of time of about 5 minutes to 4 hours at said maximum temperature; and (c) the antihistamine tannate resulting from step (b) freeze-dried at a temperature and at a reduced pressure and for such period of time that (i) at least about 90 wt. % of the water is removed from the antihistamine tannate and (ii) decomposition of the antihistamine tannate will be limited to a maximum of about 5 wt. %.

The '415 patent discloses a three-step method that results in the production of pure antihistamine tannate compositions having a minimum purity level of at least 90 wt. %, usually at least 95 wt. % and often at least 98 wt. %, based on the weight of the composition, with a yield of at least about 90% and often with a yield in excess of 97%. The chief "impurity" present in the compositions prepared by the process of the '415 patent is water which is present in an amount of 1–5 wt. %, based on the weight of the composition.

Although the process disclosed in the '415 patent represents a dramatic improvement leading to very pure antihistamine tannate compositions, it has several drawbacks: freeze-drying is quite time-consuming (typically 30–36 hours to remove 1 liter of water) and expensive and requires specialized equipment in order to achieve the reduced pressures and temperature required to dry the antihistamine tannate composition, i.e., a pressure of not greater than about 500 milliTorr and a temperature in the range of about −60° C. to −20° C. Such specialized equipment also limits the amount of product that can be processed within a reasonable amount of time.

It has now been found that by the process of this invention, it is possible to convert pseudoephedrine into pseudoephedrine tannate and unexpectedly, the pseudoephedrine does not undergo racemization in the course of its conversion to the tannate. This was quite surprising since a similarly useful antihistamine, e.g., levo-phenylephrine, undergoes racemization when it is reacted with tannic acid by the hot melt process of the invention to produce the tannate salt.

DETAILED DESCRIPTION OF THE INVENTION

In accordance with the process of the invention, pseudoephedrine tannate is prepared by reacting pseudoephedrine free base with tannic acid. If the pseudoephedrine is present in the form of a salt (typically a hydrochloride), the salt is neutralized with a stoichiometric amount of a base such as aqueous sodium or potassium hydroxide (e.g., 10 wt % concentration and the resulting pseudoephedrine layer is washed free of salts. The pseudoephedrine free base is heated to a temperature of about 50 to about 115° C., preferably 80 to 100° C., and tannic acid is slowly added, while mixing, to the pseudoephedrine free base over a period of a few minutes to about one hour. Reaction temperatures at or above the melting point of the free base, i.e., at or above 118° C., should be avoided since such higher reaction temperatures will result in decomposition. The reaction mixture is continuously stirred while maintaining such temperature range for a period of about 10 minutes to about 2 hours. Thereafter, the reaction mixture is cooled to room temperature. If the process is carried out with the tannic acid utilized neat, the resultant product need not be dried (it will, however, contain 1–3 weight percent of water since the tannic acid as commercially available contains 5–10 wt. % water). After any desired drying, the product is preferably milled to form a free-flowing powder preferably to a particle size of about 50 to about 200 mesh.

As mentioned above, the tannic acid may be utilized neat, i.e., no additional diluent or solvent is employed during the reaction. However, the reaction mixture without any added water is very viscous. Therefore, water, e.g., 5–30 wt. %, may be added to facilitate the stirring of the reaction mass. If desired, any such added water may ultimately be removed from the reaction product in a separate step by well-known processes, e.g., drying under vacuum (about 1 mm Hg) at about 65 to about 75° C. for 1–10 hours or more, sparging with nitrogen for 1 to 10 hours or more, etc.

The molar ratio of the pseudoephedrine free base to the tannic acid is generally in the range of about 4 to about 8, preferably 5 to 6, moles of pseudoephedrine free base per mole of tannic acid.

The pseudoephedrine tannate prepared by the process of the invention will have a softening point which is inversely related to the moisture content (as determined by Karl Fischer analysis) as may be seen from the following table:

| Softening Point, ° C. | Moisture Content, % (K.F.) |
|---|---|
| 55–60 | 9.8 |
| 82–87 | 5.9 |
| 98–102 | 2.0 |

The pseudoephedrine tannate prepared by the process of the invention may be prepared for administration in the form of pharmaceutically acceptable compositions such as powders, capsules, elixirs, syrups, nasal sprays, etc.

Tablets containing the pseudoephedrine tannate may be prepared in a conventional manner by the addition of suitable pharmaceutical carriers, including fillers, diluents, lubricants and the like as well as conventional and well known binding and disintegrating agents. A typical tablet composition of the present invention will contain, in addition to the pseudoephedrine tannate, microcrystalline cellulose, corn starch, magnesium stearate, croscarmellose sodium and coloring matter.

The suspension formulations of the pseudoephedrine tannate will typically additionally contain citric acid, caramel, glycerin, sorbitol solution, propylene glycol, saccharin sodium, sodium benzoate, flavoring agent and purified water.

If desired, the pseudoephedrine tannate prepared by the process of the invention may be formulated with other pharmaceutically active ingredients such as expectorants, antihistamines and antitussives, e.g., dextromethorphan, chlorpheniramine, dextrochlor-pheniramine, brompheniramine, dextrobrompheniranine, pyrilamine, phenylephrine, carbetapentane, guaifenesin, and the like. Typically, these other active ingredients may be employed in the form of their free bases or as their salts, e.g., citrates, maleates, hydrobromides, hydrochlorides, tannates, etc.

The following nonlimiting examples shall serve to illustrate the present invention. Unless otherwise indicated, all parts and percentages are on a weight basis.

EXAMPLE 1

The following ingredients were employed in this example:

35.4 g (0.02 mole) tannic acid (4% moisture by K. F.)

16.5 g (0.1 mole) pseudoephedrine 10 g (18% of total mass) water

The tannic acid and the water were placed in a 250 ml beaker and the temperature was raised to 90–95° C., with stirring. Thereafter, the pseudoephedrine was added, in small aliquot portions, to the reaction mixture, while stirring over a 30 minute period. After all of the pseudoephedrine had been added, the reaction mixture was stirred for one hour, while maintaining the temperature at 90° C. The resultant brown, thick slurry was then poured into a glass dish and allowed to cool overnight. The reaction product was then pulverized into a powder which had a softening point of 55–60° C. and a moisture content of 9.8% (K. F.). The powder was then dried in a vacuum oven at about 1 mm Hg at about 1 mm Hg for two hours. The dried product had a softening point of 82–87° C., and a moisture content of 5.9% (K. F.). The dried product was then further dried for an additional two hours at about 1 mm Hg at about 1 mm Hg. This further-dried product had a softening point of 98–102° C., and a moisture content of 2.0% (K. F.).

The base assay of the further dried product was 31.5% as is (32.1% on an anhydrous basis). To test the degree of reaction completeness, a two gram aliquot sample of the further-dried product was placed in 110 g of methylene dichloride, stirred and filtered. The solid weighed 2.0012 g. The filtrate was evaporated to dryness, leaving a residue of 0.0051 g. The degree of completeness of the reaction was determined to be 99.75% as determined from the following equation:

100−(0.0051/2.0012)×100=99.75

EXAMPLE 2

Example 1 was repeated at an initial reaction temperature of about 115–120° C. After the pseudoephedrine had been added, the reaction mixture was maintained at a temperature of 120° C. It was observed that gaseous fumes emanated. It appeared that the pseudoephedrine was decomposing, probably to methylamine. The reaction product was then discarded. This example shows that the reaction temperature should be maintained below the melting point (118° C.) of the pseudoephedrine.

What is claimed is:

1. A method for preparing pseudoephedrine consisting essentially of reacting pseudoephedrine free base with tannic acid neat or in the additional presence of up to about 30 wt % water at a temperature of about 80 to about 115° C. and thereafter recovering the pseudoephedrine tannate.

2. The method of claim 1 wherein the pseudoephedrine free base a employed in an amount of about 4 to about 8 moles of the free base per mole of tannic acid.

3. The method of claim 2 wherein the pseudoephedrine free base is employed in an amount of 5 to 6 moles of the free base per mole of tannic acid.

4. The method of claim 1 wherein the recovered pseudoephedrine tannate is subsequently dried under vacuum at a temperature of about 50 to about 75° C. for period of 1 to 10 hours or more.

5. The method of claim 1 wherein the recovered pseudoephedrine tannate is dried by sparging with nitrogen for a period of 1 to 10 hours or more.

6. The method of claim 1 wherein the recovered pseudoephedrine tannate is milled to provide a free-flowing powder.

7. The method of claim 6 wherein the powder has a particle size in the range of about 50 to about 200 mesh.

* * * * *